United States Patent
Poigny et al.

(10) Patent No.: US 9,993,417 B2
(45) Date of Patent: Jun. 12, 2018

(54) COMBINATION OF A HYALURONIC ACID AND OF A SULPHATED POLYSACCHARIDE

(71) Applicant: PIERRE FABRE DERMO-COSMETIQUE, Boulogne-billancourt (FR)

(72) Inventors: Stéphane Poigny, Saubens (FR); Hélène Hernandez-Pigeon, Cugnaux (FR); Jean-Hilaire Saurat, Geneva (CH); Gürkan Kaya, Geneva (CH)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 0 days. days.

(21) Appl. No.: 15/307,681

(22) PCT Filed: Apr. 30, 2015

(86) PCT No.: PCT/EP2015/059544
§ 371 (c)(1),
(2) Date: Oct. 28, 2016

(87) PCT Pub. No.: WO2015/166063
PCT Pub. Date: Nov. 5, 2015

(65) Prior Publication Data
US 2017/0049678 A1 Feb. 23, 2017

(30) Foreign Application Priority Data
Apr. 30, 2014 (FR) ..................... 14 53973

(51) Int. Cl.
| A61K 8/73 | (2006.01) |
| A61K 31/728 | (2006.01) |
| A61K 31/737 | (2006.01) |
| A61Q 19/08 | (2006.01) |
| A61K 45/06 | (2006.01) |
| A61K 31/11 | (2006.01) |
| A61K 31/7048 | (2006.01) |
| A61K 8/33 | (2006.01) |
| A61K 8/67 | (2006.01) |
| A61K 9/00 | (2006.01) |

(52) U.S. Cl.
CPC ............... *A61K 8/735* (2013.01); *A61K 8/33* (2013.01); *A61K 8/678* (2013.01); *A61K 8/73* (2013.01); *A61K 9/0014* (2013.01); *A61K 31/11* (2013.01); *A61K 31/7048* (2013.01); *A61K 31/728* (2013.01); *A61K 31/737* (2013.01); *A61K 45/06* (2013.01); *A61Q 19/08* (2013.01); *A61K 2800/5922* (2013.01)

(58) Field of Classification Search
CPC .... A61K 8/735; A61K 31/728; A61K 31/737; A61Q 19/08
See application file for complete search history.

(56) References Cited

U.S. PATENT DOCUMENTS

| 5,925,626 | A * | 7/1999 | della Valle ........... A61K 9/0014 514/54 |
| 6,559,131 | B1 * | 5/2003 | Senni .................... A61K 31/737 435/195 |
| 6,569,906 | B1 * | 5/2003 | Redoules ............... A61K 8/602 514/451 |
| 6,572,868 | B1 | 6/2003 | Cope |
| 2007/0172442 | A1 * | 7/2007 | Saurat .................... A61K 8/671 424/70.13 |
| 2009/0286756 | A1 | 11/2009 | Ciancia et al. |
| 2010/0316683 | A1 | 12/2010 | Piron et al. |
| 2014/0271881 | A1 | 9/2014 | Allart et al. |

FOREIGN PATENT DOCUMENTS

| EP | 1 987 153 B1 | 1/2011 |
| WO | WO 96/06622 A1 | 3/1996 |
| WO | WO 2008/068297 A1 | 6/2008 |
| WO | WO 2008/071245 A1 | 6/2008 |
| WO | WO 2010/086197 A1 | 8/2010 |
| WO | WO 2011/109469 A1 | 9/2011 |
| WO | WO 2013/017807 A1 | 2/2013 |
| WO | WO 2013/150253 A1 | 10/2013 |

OTHER PUBLICATIONS

Loeffler, Markus, et al. "Targeting tumor-associated fibroblasts improves cancer chemotherapy by increasing intratumoral drug uptake." Journal of Clinical Investigation 116.7 (2006): 1955.*
European Pharmacopoeia 7.0, "Sodium Hyaluronate," vol. 1472, Jan. 2011, pp. 2927-2929.
Podzimek et al., "Solution Properties of Hyaluronic Acid and Comparison of SEC-MALS-VIS Data with Off-line Capillary Viscometry," J. of Applied Polymer Science, vol. 116, 2010 (Published online Feb. 4, 2010), pp. 3013-3020.
Tammi et al., "Hyaluronan Metabolism in Skin," Progress in Histochemistry & Cytochemistry, vol. 29, No. 2, 1994, pp. 1-81.
Toole, "Hyaluronan: From Extracellular Glue to Peracellular Cue," Nat. Rev. Cancer, vol. 4, No. 7, Jul. 2004, pp. 528-539 (Total 13 pages).
Witte et al., "General Principles of Wound Healing," Surg. Clin. North Am., vol. 77, No. 3, Jun. 1997, pp. 509-528.
International Search Report issued in PCT/EP2015/059544, dated Jul. 13, 2015.
Written Opinion of the International Searching Authority (PCT/ISA/237) issued in PCT/EP2015/059544, dated Jul. 13, 2015.
Commercial Brochure of Ascophyscient, Algues & Mer Cosmetics, dated Dec. 2011.

* cited by examiner

*Primary Examiner* — Bethany P Barham
*Assistant Examiner* — Peter Anthopolos
(74) *Attorney, Agent, or Firm* — Birch Stewart Kolasch & Birch, LLP

(57) ABSTRACT

The present invention relates to a combination comprising a hyaluronic acid or a salt thereof and a sulphated polysaccharide of which the molecular weight is between 5 and 25 kDa, which is of use in particular for combating the signs of skin ageing or for treating and healing skin wounds.

12 Claims, 2 Drawing Sheets

COMBINATION OF A HYALURONIC ACID AND OF A SULPHATED POLYSACCHARIDE

FIELD OF THE INVENTION

The present invention relates to a novel combination of a hyaluronic acid or a salt thereof and of a low-molecular-weight sulphated polysaccharide; and to the use of said combination in the fields of anti-aging and healing.

PRIOR ART

Hyaluronic acid (HA) is a molecule with the most important role in the skin. It is indeed the principal component of the extracellular matrix. The latter refers to the set of extracellular macromolecules of the connective tissue. It is mainly made up of glycoproteins, pure proteins as well as glycosaminoglycans. HA is a linear non-sulphated glycosaminoglycan composed of repeating disaccharide units themselves composed of D-glucuronic acid and N-acetyl-D-glucosamine linked with alternating β1-3 and β1-4 glycosidic bonds between the dimers (Tammi R., Agren U. M., Tuhkanen A. L., Tammi M. Hyaluronan metabolism in skin. Progress in Histochemistry & Cytochemistry 29(2):1-81, 1994). In its native form, HA is a polymer having a very high molecular weight between 600,000 Da and 3 MDa (Toole B P. Hyaluronan: from extracellular glue to peracellular cue. Nat Rev Cancer 2004, 4:538-539).

With age, HA decreases in amount and in degree of polymerization, resulting in less water retained in the extracellular matrix. The skin then undergoes an aging process which leads to increased fibrosis and to a drop in elastic fiber content. During the aging process, a modification of skin structure and functions are observed. This aging is physiological in nature but can be also photoinduced, i.e. due to repeated exposure of the skin to sunlight, in particular ultraviolet light. The principal clinical signs of skin aging are the appearance of lines and deep wrinkles, which obviously increase with age. The furrows and wrinkles are marked; the skin becomes hollow and loses its firmness; on the surface, the skin loses its radiance.

Sulphated polysaccharides comprise, inter alia, sulphated fucans and sulphated ulvans having a molecular weight between 5 and 25 kDa.

These low-molecular-weight sulphated polysaccharides have advantageous biochemical properties: inhibition of degradation of collagen and elastin, restructuring, anti-inflammatory action, and induction of HA production.

During aging, fibroblasts enter senescence and their ability to proliferate greatly decreases. Thus, the fact of being able to stimulate the proliferation of these cells anew is one of the pathways studied for combating skin aging.

Furthermore, wound healing is a complex and dynamic biological process which brings into play the interaction of numerous local and systemic factors in normal tissue repair. Healing progresses in three interdependent phases: hemostasis and inflammation, proliferation and remodeling (General principles of wound healing. Witte M B, Barbul A. Surg Clin North Am. 1997 June; 77(3):509-28.). Proliferation involves three clearly observable processes: granulation, contraction and re-epithelialization.

During granulation, one observes the proliferation and migration toward the wound bed of cells which will intervene in the rest of the repair process. Thus, macrophages, fibroblasts and endothelial cells are found there. Macrophages constantly release chemotactic factors and growth factors. Fibroblasts construct the new cellular matrix necessary to cell growth at the base of the wound. This scaffolding supports cell migration. Lastly, endothelial cells trigger the formation of vascular buds which will constitute new capillaries, which will restore perfusion and ensure the supply of oxygen and of nutrients essential to the metabolic activity of cells in the wound.

Wound contraction is a mechanism of reducing wound size, and fibroblasts play a leading role in this contraction.

Re-epithelialization consists in the regeneration of an epidermis that covers a wound to form an effective barrier against the external environment, capable of becoming pigmented and of recovering its sensory and immune functions. It thus involves the cellular processes of keratinocyte migration and proliferation, but also the differentiation of this neo-epithelium and the restoration of a basal membrane that connects the dermis and the epidermis. When the migration of basal cells in the direction of the center of the wound enables the two wound edges to meet, a wave of cell mitosis occurs to fill the spaces left by the migration and to provide cells for the epithelial tissue in three-dimensional regeneration.

The stages of proliferation of keratinocyte cells, fibroblasts or endothelial cells can be regarded as one of the functional phenomena showing the healing activity of an active agent. Increased fibroblast proliferation would participate in the healing of a deep wound (reaching the dermis), whereas increased keratinocyte proliferation would participate in re-epithelialization.

There remains a need to propose novel cosmetic compositions for combating the signs of skin aging.

The Applicant has shown the existence of synergy between hyaluronic acid and a low-molecular-weight sulphated polysaccharide on fibroblast proliferation. This activity is particularly advantageous in the field of anti-aging but also in tissue regeneration and in healing skin lesions.

DETAILED DESCRIPTION

The present invention has as an object a combination comprising a hyaluronic acid or a salt thereof and a sulphated polysaccharide having a molecular weight between 5 and 25 kDa.

In the context of the present invention, the terms "hyaluronic acid", "hyaluronic acid fragments", "HA" and "hyaluronan" are used interchangeably to refer to hyaluronic acid. When hyaluronic acid is in salt form, it is referred to as hyaluronate.

In a particular embodiment of the invention, the combination comprises a hyaluronic acid or a salt thereof the weight average molecular weight (Mw) of which will be between 50,000 and 750,000 Da.

In a particular embodiment of the invention, the HA fragment or a salt thereof is characterized by a weight average molecular weight between 60 and 120 kDa, said molecular weight being measured by an analytical method combining size-exclusion chromatography (SEC) with a multi-angle light scattering photometer (MALS) coupled with a viscometer (VIS) and a differential refractometer (RI).

In a particular embodiment, it will be sodium hyaluronate.

The molecular weight of the HA or a salt thereof can be measured using the method of the European Pharmacopoeia which measures intrinsic viscosity with a Ubbelohde capillary viscometer (see European Pharmacopoeia 7.6, sodium hyaluronate monograph ref. 01/2011:1472). This viscosity value is then related to average molecular weight by the Mark-Houwink relationship. This method is long and requires perfect reproducibility.

In the context of the present invention, the weight average molecular weight of the HA or a salt thereof is measured by the SEC-MALS-VIS-RI method, which is an analytical method combining size-exclusion chromatography (SEC) with a multi-angle light scattering photometer (MALS) coupled with a viscometer (VIS) and a differential refractometer. This technique makes it possible to obtain the weight average molecular weight (Mw).

This technique makes it possible to characterize the molecular weights of HAs in a precise and reproducible manner (Stepan Podzimek & al. Solution of Hyaluronic Acid and Comparison of SEC-MALS-VIS Data with Off-line Capillary Viscometry. Journal of Applied Polymer Science. 2009).

Coupling size-exclusion chromatography (SEC) with a MALS detector makes it possible, after injecting a polymer solution in a chromatographic system, to separate these polymers by size in the chromatographic column, to measure this size by light scattering and to quantify them using a differential refractometer or a UV spectrometer.

Hyaluronic acid or a salt thereof is solubilized in aqueous 0.1 M NaCl solution then eluted on a column filled with polystyrene-divinylbenzene beads having a calibrated pore size. Large polymer chains do not pass into all the pores and are thus eluted before small chains.

The MALS detector measures the scattering of incident light at various angles. These angles make it possible, by extrapolation, to measure $R_0$, which is the scattering at angle 0. $R_0$ is directly proportional to molecule size.

The $S_i$ response of the differential refractometer is proportional to the total mass $C_i$ of the polymer having degree of polymerization i according to the following equation (1):

$$S_i = K' \cdot dn/dc \cdot C_i$$

where: $S_i$ is thus the response of the differential refractometer,

K' is a constant linked to the apparatus, and $C_i$ is the total mass (weight) of the polymer having degree of polymerization i ($C_i = N_i \times M_i$), $N_i$ being the number of chains of molar mass $M_i$.

The refractive index increment dn/dc is in addition a specific value of the polymer under study.

This dn/dc ratio can be measured according to the following protocol exemplified with sodium hyaluronate.

a/ Apparatus and Preparation of Solutions:

Measurements are taken on a refractometer such as the Brice-Phoenix model having as incident light source a helium-neon laser ($\lambda$=633 nm).

Various polymer concentrations to be studied are prepared independently by weighing (duration in solution=24 hours). The respective refractive indices (dn) are then measured using the refractometer.

b/ Result

The results are presented in the form of a graph dn=f (concentration) (see FIG. 1). A linear regression of type Y=A+B*X is then determined.

In the case of sodium hyaluronate, the values A and B determined are respectively A=−2.030 and B=14927.911.

The dn/dc ratio thus corresponds to k×B where k is the constant of the apparatus which is equal to $0.97 \cdot 10^{-5}$ in this example.

For sodium hyaluronate, dn/dc is thus evaluated at $0.97 \cdot 10^{-5} \times 14927.911 = 0.145$ ml/g.

The following formula gives the relationship between all the measured parameters:

$$R_0 = K \cdot C_i \cdot M_i$$

where: $R_0$ is the Rayleigh ratio at the scattering angle 0,

K is the constant of the apparatus, $C_i$ is the total mass of the polymer having degree of polymerization i [calculated according to equation (1)] of the injected solution, and $M_i$ is the molar mass of the polymer chain sought.

The weight average molecular weight Mw can then be calculated according to the formula:

$$Mw = \Sigma C_i M_i / \Sigma C_i.$$

All the molecular weights are expressed in daltons.

Hyaluronic acid or a salt thereof, object of the present invention, can be obtained according to one of the processes known to persons skilled in the art, such as those mentioned in the document EP1987153.

HA is obtained mainly, in an industrial manner, by bacterial fermentation: hyaluronic acid filaments are synthesized by bacteria.

Thus in a particular embodiment of the invention, a native HA having a high molecular weight ranging generally from 1 MDa to 2 MDa is obtained by bacterial fermentation using a selected bacterial strain.

The polymer obtained can then be separated from the bacterium. The solution is then purified and then hydrolyzed by controlled acid hydrolysis until the desired molecular weight is obtained.

In the case of preparation of sodium hyaluronate, one will proceed to a neutralization step by adding NaOH.

The hyaluronic acid salt will preferentially be sodium hyaluronate.

In the context of the present invention, low-molecular-weight sulphated polysaccharides can be selected from sulphated fucans and sulphated ulvans having a molecular weight between 5 and 25 kDa.

Sulphated fucans are polysaccharides comprising sulphated L-fucose. These polysaccharides can be extracted in particular from brown algae, for example from the order Fucales or Laminariales.

Sulphated ulvans are sulphated anionic polysaccharides comprising uronic acids (e.g. glucuronic acid, iduronic acid) and sugars capable of being sulphated (e.g. 3-sulphate rhamnose, galactose, xylose, glucose) distributed in repeated motifs. The principal motifs are:

ulvanobiuronic acid 3-sulphate type A consisting of 3-sulphate α-L-rhamnose linked with β-D-glucuronic acid by a 1→4 type bond, and ulvanobiuronic acid 3-sulphate type B consisting of 3-sulphate α-L-rhamnose linked with α-L-iduronic acid by a 1→4 type bond.

Ulvans can be extracted in particular from green algae of type ulva or enteromorpha (*Ulva* sp. and *Enteromorpha* sp.).

According to a particular embodiment, the low-molecular-weight sulphated fucan is as described in WO 2010/086197.

Mention may be made of the proprietary commercial product Ascophyscient® (Algues et Mer) extracted from the alga *Ascophyllum nodosum*.

According to another particular embodiment, the low-molecular-weight sulphated ulvan is as described in WO 2013/150253.

Mention may also be made of the fraction QT40® marketed by Green Tech based on a particular oligosaccharide from the alga *Ulva lactuca*: a sulpho-oligorhamnoglucuronan.

According to a particular embodiment of the invention, the mass ratio of hyaluronic acid to polysaccharide is between 0.1 and 10.

According to another particular embodiment of the invention, the mass ratio of hyaluronic acid to polysaccharide is between 0.5 and 5, and preferably between 0.5 and 2.

The present invention further relates to a combination of hyaluronic acid or a salt thereof and of a low-molecular-weight sulphated polysaccharide according to the invention (i.e. having a molecular weight between 5 and 25 kDa) for use to promote fibroblast proliferation.

The present invention also relates to a cosmetic composition comprising, as an anti-aging active ingredient, a combination of a hyaluronic acid or a salt thereof and of a sulphated polysaccharide having a molecular weight between 5 and 25 kDa and further comprising at least one cosmetically acceptable excipient.

Preferably, the cosmetically acceptable excipients are suited to topical administration.

Acceptable excipients make it possible in particular to ensure good stability and a pleasant texture and feel. They can also be, for example, formulation agents or additives of known and conventional use in cosmetics: mention may be made of surfactants, colorants, preservatives, fragrances, film-forming agents, thickeners, etc.

The anti-aging compositions can be in the forms commonly known for topical administration on the skin, i.e. in particular creams, emulsions, lotions, serums, masks, wrinkle fillers, eye liners, etc.

The object of the present invention is directed at the cosmetic use of the combination according to the present invention or of this cosmetic composition according to the invention for combating the signs of skin aging. The cosmetic use of the combination according to the present invention or the cosmetic composition according to the invention is more particularly intended to restore matter to the skin, to strengthen the firmness thereof and to visibly reduce marked wrinkles and deep furrows.

The present invention also relates to a method for combating the signs of skin aging comprising the administration, preferably topically, of an effective amount of a combination according to the invention or of a cosmetic composition according to the invention to a person in need thereof.

Another object of the present invention relates to a dermatological composition intended to accelerate skin repair in order to restore the integrity and the quality of the skin, comprising as dermatological or cosmetic active ingredient the combination of a hyaluronic acid or a salt thereof and of a sulphated polysaccharide the molecular weight of which is between 5 and 25 kDa mentioned above and further comprising at least one dermatologically or cosmetically acceptable excipient.

In a preferred embodiment of the invention, the composition is intended for topical application.

Dermatologically (pharmaceutically) or cosmetically compatible excipients can be any excipient among those known to persons skilled in the art for obtaining a composition for topical application in the form of a milk, a cream, a balm, an oil, a lotion, a gel, a foaming gel, an ointment, a spray, etc.

In a preferred embodiment, the composition will be in the form of a cream or an ointment.

In a particular embodiment, the dermatological and cosmetic compositions according to the invention comprise at least one other active ingredient.

This other active ingredient could in particular be selected from the group comprising anti-aging agents, healing agents, soothing agents, antipruritic agents, antioxidants, anti-radical agents, anti-UV agents, agents stimulating the synthesis of dermal macromolecules or energy metabolism, hydrating agents, depigmenting agents, antibacterials, antifungals, anti-inflammatories, or anesthetics.

According to a particular embodiment, the compositions according to the invention, preferably cosmetic, further comprise retinaldehyde. This supplementary anti-aging active agent is a direct precursor of retinoic acid for an immediate cellular metabolism reactivator effect. Retinaldehyde increases the expression of HA receptors, CD44, and induces HA synthesis.

The composition according to the invention then comprises a combination of hyaluronic acid or a salt thereof, of low-molecular-weight sulphated polysaccharide and of retinaldehyde. Such a combination has a restructuring and redensifying effect in the dermo-epidermal junction and the papillary dermis.

According to another embodiment of the invention, the composition will further comprise a tocopherol derivative including delta-tocopheryl-glucopyranoside: its powerful antioxidant effects protect the skin and preserve the radiance thereof.

The composition according to the invention then comprises a combination of hyaluronic acid or a salt thereof, of low-molecular-weight sulphated polysaccharide and of delta-tocopheryl-glucopyranoside.

According to another particular embodiment, the other active ingredient will be selected from healing agents, soothing agents and mixtures thereof. Such an active ingredient will be used preferably in dermatological compositions.

Lastly, another object of the present invention is directed at a combination of hyaluronic acid or a salt thereof and of low-molecular-weight sulphated polysaccharide or a dermatological composition containing same according to the invention for use as a medicine (more particularly a dermatological medicine), intended in particular for treating and healing skin lesions.

The present invention also relates to the use of a combination of a hyaluronic acid or a salt thereof and of a sulphated polysaccharide having a molecular weight between 5 and 25 kDa for the preparation of a medicine (more particularly a dermatological medicine), intended in particular for treating and healing skin lesions.

The present invention also relates to a method for treating and healing skin lesions comprising the administration, preferably topical, of an effective amount of a combination of a hyaluronic acid or a salt thereof and of a sulphated polysaccharide having a molecular weight between 5 and 25 kDa or a dermatological composition containing same according to the invention to a person in need thereof.

The dermatological and cosmetic compositions according to the invention are intended in particular for the care of skin injured:

following invasive procedures/treatments: surgical procedures (exeresis, shaving) with or without suture, cryotherapy, laser ablation, moderate or heavy peeling, mesotherapy, curettage, post-traumatically with superficial cuts or burns,
following superficial (noninvasive) procedures requiring a healing product which accelerates skin recovery, for long-term use (until complete repair of the skin),
following mild external damage: superficial abrasions, sunburn.

The treatment of lesions of the skin and the mucous membranes according to the invention may in particular comprise the treatment of cuts, sutures, abrasions, scratches, scrapes, scars following surgery or following an aesthetic dermatology procedure, superficial burns, sunburn.

The present invention further relates to the use of a cosmetic composition according to the invention intended to improve healing and skin repair.

The invention will be better understood upon reading the results below which illustrate the invention without limiting the scope thereof.

FIGURES

EXAMPLES

Pharmacological Evaluation of the Combination of a Sodium Hyaluronate Fragment Having a Weight Average Molecular Weight Between 60 and 120 kDa (HAF120) and of a Sulphated Fucan Having a Low Molecular Weight (5-25 kDa) on Fibroblast Proliferation Protocol:

The technique used is that of incorporation of a nucleotide, 5-bromo-2'-deoxyuridine (BrdU), a thymidine analog, in the DNA of S-phase cells, at 37° C. This technique makes it possible to quantify cells of which the advance in the cell cycle is characteristic of a proliferating cell (S-phase or DNA synthesis phase).

Normal human fibroblasts (NHF), isolated from surgical waste skin, are usually cultivated in Dulbecco's modified Eagle's medium (DMEM) with 10% fetal calf serum (FCS). In our experimental conditions, dilutions of the products to be tested are prepared in DMEM with 3% FCS.

The cells are first deprived of FCS for 24 hours to stop cell multiplication before incubating them in the presence of the molecules to be evaluated for 44 hours at 37° C., in a 5% $CO_2$ atmosphere.

BrdU incorporation, proportional to cell proliferation rate, is evaluated by an anti-BrdU antibody system (Roche Applied Science). The corresponding absorbance (OD) is measured at 450 nm. This datum is thus proportional to cell proliferation rate.

The active agents evaluated are as follows:
Positive control: epidermal growth factor (EGF) at 10 ng/ml
Proprietary commercial product Ascophyscient® (Algues et Mer): 10 and 100 µg/ml (corresponding to 0.001% and 0.01%, respectively)
60-120 kDa sodium hyaluronate according to Example 1: 100 and 1000 µg/ml (corresponding to 0.01 and 0.1%, respectively)
Combination comprising respectively Ascophyscient® and 60-120 kDa sodium hyaluronate at the following respective concentrations:
10 µg/ml+100 µg/ml,
10 µg/ml+1000 µg/ml.
Analysis of the Results:
expressed as OD (proportional to BrdU incorporation and thus to cell proliferation rate)
expressed as percent stimulation:

$$\left[\frac{OD \text{ treated}}{OD \text{ control}} \times 100\right] - 100$$

expressed as standard error of the mean: SEM=standard deviation (SD)/$\sqrt{n}$
Statistical Analyses:
Statistical analyses using unpaired bilateral Student's t-test were carried out on the raw OD values.

Figure 1:
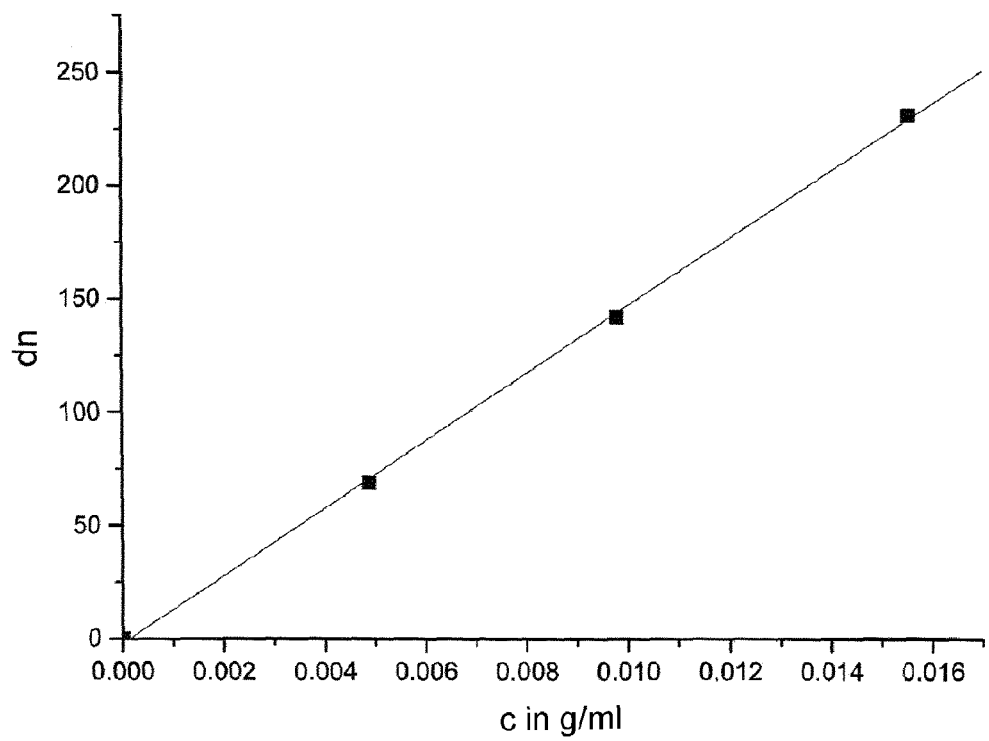
FIG. 1 shows refractive index dn as a function of concentration c for sodium hyaluronate.
Figure 2:
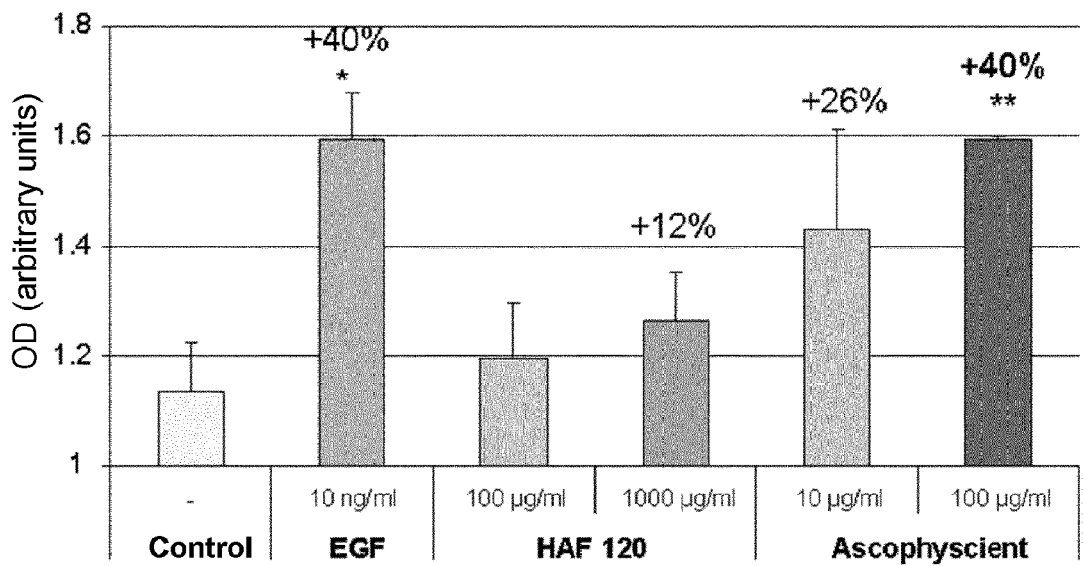
FIG. 2 shows the effect of HA according to invention (HAF120) at 100 and 1000 µg/ml and of Ascophyscient® at 10 and 100 µg/ml on fibroblast proliferation. *: p<0.05 and **: p<0.01. Experiment representative of three independent experiments.
Figure 3:
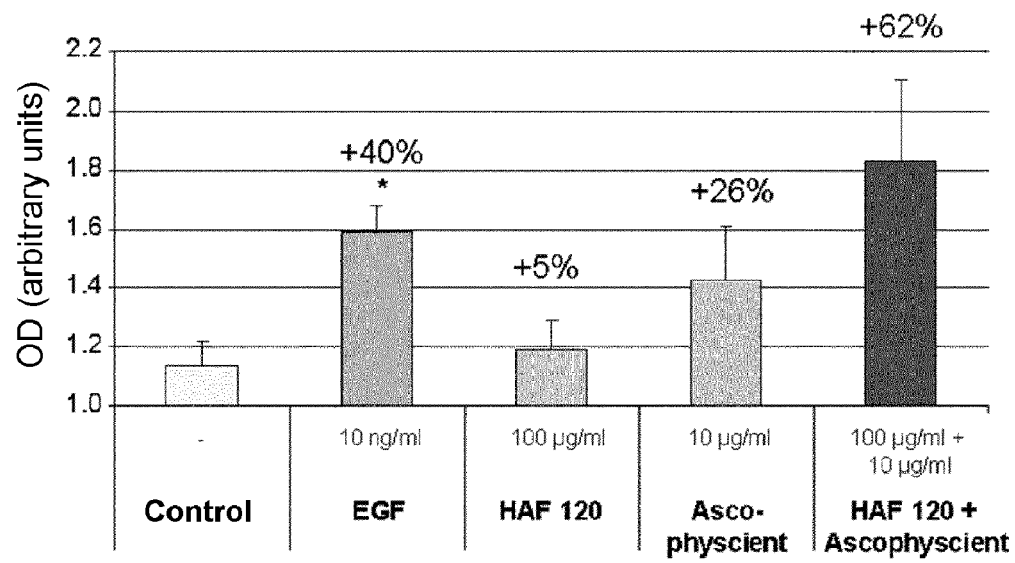
FIG. 3 shows the effect of HA according to invention (HAF120) at 100 µg/ml, Ascophyscient® at 10 µg/ml and a combination thereof on fibroblast proliferation. *: p<0.05. Experiment representative of three independent experiments.
Figure 4:
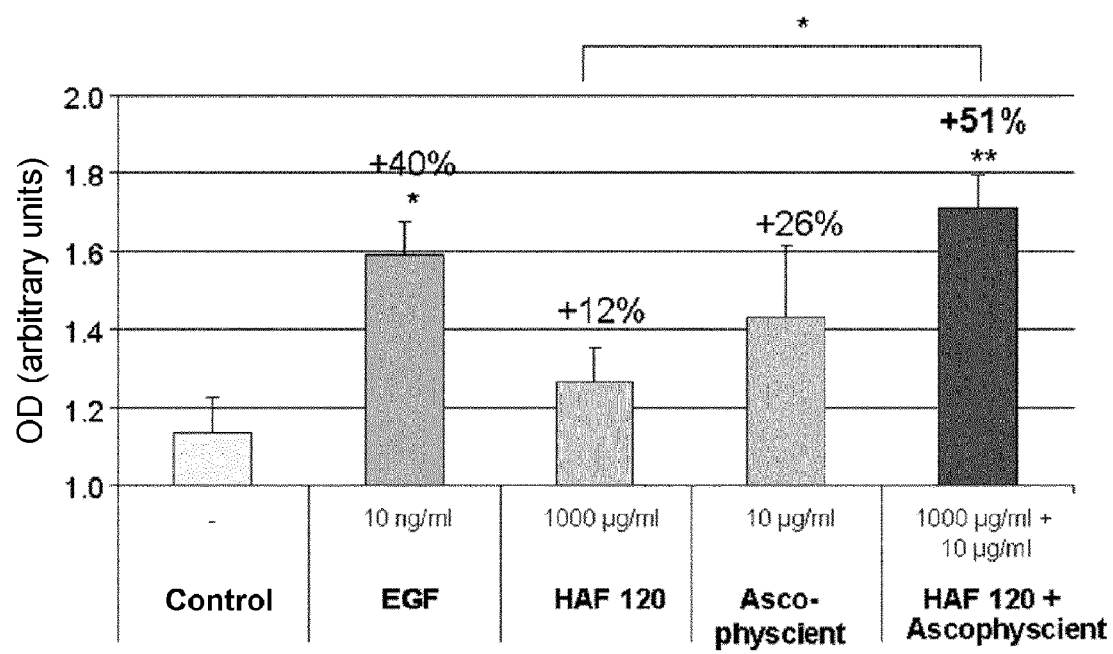
FIG. 4 shows the effect of HA according to invention (HAF120) at 1000 µg/ml, Ascophyscient® at 10 µg/ml and a combination thereof on fibroblast proliferation. *: p<0.05 and **: p<0.01. Experiment representative of three independent experiments.

This test then gives p-values characterizing the significance of the results obtained for the various conditions. The degree of significance is established as follows:
significant for p<0.05 (*)
very significant for p<0.01 (**)
highly significant for p<0.001 (***)
not significant for p>0.05
Results:
In these experimental conditions,
Ascophyscient® induced fibroblast proliferation in a very reproducible and statistically significant manner, especially at 100 µg/ml (FIG. 2).
Sodium hyaluronate alone has a moderate effect on fibroblast proliferation (FIG. 2).
The combination of these two compounds induced fibroblast proliferation in a synergistic manner (FIGS. 3 and 4).
Conclusions:
In these experimental conditions, Ascophyscient® induced fibroblast proliferation in a very reproducible and statistically significant manner. The combination of Ascophyscient® with HAF120 induced fibroblast proliferation in a synergistic manner.

By inducing fibroblast proliferation, Ascophyscient® and the combination thereof with the 60-120 kDa sodium hyaluronate fragment restores cellular metabolism and participates in dermal repair and in combating aging.

EXEMPLARY COMPOSITIONS

Example 1

| Name | Percentage |
| --- | --- |
| Purified water | q.s. 100% |
| Glycerin | 6 |
| Disodium EDTA | 0.1 |

-continued

| Name | Percentage |
| --- | --- |
| Phenoxyethanol | 0.35 |
| Acrylates/C10-30 Alkyl Acrylate Crosspolymer (Carbopol ® Ultrez 21) | 0.4 |
| Polyacrylate-13 & Polyisobutene & Polysorbate 20 & Water (Sepiplus ™ 400) | 1 |
| Glyceryl Stearate & PEG-100 Stearate (Simulsol ™ 165) | 4 |
| Cetyl Alcohol | 1 |
| Caprylic/Capric Triglycerides (Myritol ® 318) | 10 |
| Dimethicone (DC 200) | 4 |
| Dicaprylyl Carbonate | 4 |
| 60-120 kDa Sodium hyaluronate according to the invention | 0.5 |
| Ascophyscient ® | 0.3 |
| Fragrance | 0.1 |

Example 2

| Name | Percentage |
| --- | --- |
| Purified water | q.s. 100% |
| Glycerin | 6 |
| Disodium EDTA | 0.1 |
| Phenoxyethanol | 0.35 |
| Acrylates/C10-30 Alkyl Acrylate Crosspolymer (Carbopol ® Ultrez 21) | 0.4 |
| Polyacrylate-13 & Polyisobutene & Polysorbate 20 & Water (Sepiplus ™ 400) | 1 |
| Glyceryl Stearate & PEG-100 Stearate (Simulsol ™ 165) | 4 |
| Cetyl alcohol | 1 |
| Caprylic/Capric Triglycerides (Myritol ® 318) | 10 |
| Dimethicone (DC 200) | 4 |
| Isododecane | 4 |
| 60-120 kDa Sodium hyaluronate according to the invention | 0.5 |
| Ascophyscient ® | 0.3 |
| Retinaldehyde | 0.05 |
| Fragrance | 0.1 |

The invention claimed is:

1. A composition comprising a hyaluronic acid or a salt thereof having a weight average molecular weight between 60 and 120 kDa and a sulphated polysaccharide having a molecular weight between 5 and 25 kDa selected from sulphated fucans.

2. The composition according to claim 1, wherein the mass ratio of the hyaluronic acid or a salt thereof to the sulphated polysaccharide is between 0.1 and 10.

3. A dermatological or cosmetic composition comprising as active ingredient a composition according to claim 1, with at least one dermatologically or cosmetically acceptable excipient.

4. The dermatological or cosmetic composition according to claim 3, further comprising another active ingredient.

5. The dermatological or cosmetic composition according to claim 4, wherein the other active ingredient is selected from antiaging agents, healing agents, soothing agents, antipruritic agents, antiradical agents, anti-UV agents, hydrating agents, depigmenting agents, antibacterials, anti-fungals, anti-inflammatories, anesthetics and mixtures thereof.

6. The dermatological or cosmetic composition according to claim 4, wherein the other active ingredient is retinaldehyde.

7. The dermatological or cosmetic composition according to claim 4, wherein the other active ingredient is delta-tocopheryl-glucopyranoside.

8. A method for combating the signs of skin aging comprising the topical administration to a person in need thereof of an effective amount of a composition according to claim 1.

9. A method for treating skin lesions comprising the topical administration to a person in need thereof of an effective amount of a composition according to claim 1.

10. A method for improving skin healing comprising the topical administration to a person in need thereof of an effective amount of a composition according to claim 1.

11. A method for combating the signs of skin aging comprising the administration to a person in need thereof of an effective amount of a cosmetic composition according to claim 3.

12. A method for treating cuts, sutures, abrasions, scratches, scrapes, scars following surgery or following an aesthetic dermatology procedure, superficial burns, or sunburn comprising the administration to a person in need thereof of an effective amount of a dermatological composition according to claim 3.

* * * * *